United States Patent
Sham

(10) Patent No.: US 10,610,145 B2
(45) Date of Patent: Apr. 7, 2020

(54) SAFETY DRIVING SYSTEM

(71) Applicant: Wellen Sham, Taipei (TW)

(72) Inventor: Wellen Sham, Taipei (TW)

(*) Notice: Subject to any disclaimer, the term of this patent is extended or adjusted under 35 U.S.C. 154(b) by 0 days.

(21) Appl. No.: 15/199,268

(22) Filed: Jun. 30, 2016

(65) Prior Publication Data

US 2018/0000397 A1   Jan. 4, 2018

(51) Int. Cl.

| | |
|---|---|
| *A61B 5/00* | (2006.01) |
| *A61B 5/18* | (2006.01) |
| *G08B 21/06* | (2006.01) |
| *G16H 40/67* | (2018.01) |
| *A61B 3/113* | (2006.01) |
| *A61B 5/01* | (2006.01) |

(Continued)

(52) U.S. Cl.
CPC .............. *A61B 5/18* (2013.01); *A61B 3/113* (2013.01); *A61B 5/0022* (2013.01); *A61B 5/0077* (2013.01); *A61B 5/01* (2013.01); *A61B 5/0402* (2013.01); *A61B 5/0476* (2013.01); *A61B 5/082* (2013.01); *A61B 5/6893* (2013.01); *A61B 5/7282* (2013.01); *G08B 21/06* (2013.01); *G08G 5/0056* (2013.01); *G08G 5/0069* (2013.01); *G16H 40/67* (2018.01)

(58) Field of Classification Search
USPC ........................................................ 702/2–5
See application file for complete search history.

(56) References Cited

U.S. PATENT DOCUMENTS

| | | | |
|---|---|---|---|
| 6,661,345 B1 | 12/2003 | Bevan et al. | |
| 7,509,212 B2 * | 3/2009 | Bodin ................. | G01C 21/005 244/190 |

(Continued)

FOREIGN PATENT DOCUMENTS

DE   10 2015 105581 A1   5/2016

OTHER PUBLICATIONS

Droitcour et al, "Signal-to-Noise Ratio in Doppler Radar System for Heart and Respiratory Rate Measurements." IEEE Transactions on Microwave Theory and Techniques, vol. 57, No. 10, Oct. 2009, 10 pages.

(Continued)

*Primary Examiner* — Michael W Kahelin
*Assistant Examiner* — Shirley X Jian
(74) *Attorney, Agent, or Firm* — Kilpatrick Townsend & Stockton, LLP

(57) ABSTRACT

A method for monitoring physical conditions of an operator of a driving apparatus is described. The method includes obtaining an identity of the operator, acquiring signals indicating a physical condition of the operator, and determining whether the physical condition as indicated by the signals has breached a predetermined threshold. Further, when it is determined that the physical condition as indicated by the signals has breached a predetermined threshold, the method includes generating a first status indicating the operator suffers an abnormal physical condition, obtaining a current location of the driving apparatus, generating a first notification based on the first status, the first notification indicating the identity of the operator and the current location of the driving apparatus, the first notification describing the first user suffers the abnormal physical condition, and transmitting the first notification to a data receiver in a healthcare facility.

18 Claims, 7 Drawing Sheets

(51) Int. Cl.
*A61B 5/0402* (2006.01)
*A61B 5/0476* (2006.01)
*A61B 5/08* (2006.01)
*G08G 5/00* (2006.01)

(56) References Cited

U.S. PATENT DOCUMENTS

| | | | |
|---|---|---|---|
| 7,666,151 B2* | 2/2010 | Sullivan | A61B 5/11 340/573.1 |
| 8,140,358 B1* | 3/2012 | Ling | G06Q 40/08 340/439 |
| 8,311,858 B2* | 11/2012 | Everett | G06Q 40/08 246/45 |
| 8,359,901 B2* | 1/2013 | Freund | G07C 5/0891 73/23.3 |
| 8,761,821 B2* | 6/2014 | Tibbitts | H04W 48/04 455/297 |
| 8,787,936 B2* | 7/2014 | Tibbitts | H04W 48/04 455/456.1 |
| 8,892,451 B2* | 11/2014 | Everett | G06Q 40/08 340/439 |
| 8,924,240 B2* | 12/2014 | Depura | H04W 52/0258 701/469 |
| 9,053,516 B2* | 6/2015 | Stempora | G06Q 40/08 |
| 9,094,816 B2* | 7/2015 | Maier | H04W 4/22 |
| 9,124,955 B2* | 9/2015 | Geva | B60K 28/066 |
| 9,141,975 B2* | 9/2015 | Meller | G06Q 30/0269 |
| 9,162,753 B1* | 10/2015 | Panto | B64C 19/00 |
| 9,440,657 B1* | 9/2016 | Fields | B60K 28/066 |
| 9,460,601 B2 | 10/2016 | Mimar | |
| 9,635,534 B2* | 4/2017 | Maier | H04W 4/70 |
| 9,682,622 B2* | 6/2017 | Kim | H04N 5/23229 |
| 9,694,771 B1 | 7/2017 | Ding | |
| 9,809,169 B1 | 11/2017 | Naboulsi | |
| 10,085,683 B1* | 10/2018 | Sham | G16H 50/20 |
| 2003/0204290 A1 | 10/2003 | Sadler et al. | |
| 2006/0167597 A1* | 7/2006 | Bodin | G01C 21/005 701/3 |
| 2006/0212195 A1* | 9/2006 | Veith | G06Q 10/06 701/33.4 |
| 2008/0074307 A1 | 3/2008 | Boric-Lubecke et al. | |
| 2008/0163670 A1 | 7/2008 | Georgeson | |
| 2008/0191863 A1* | 8/2008 | Boling | G08B 25/08 340/521 |
| 2009/0293589 A1* | 12/2009 | Freund | G07C 5/0891 73/23.3 |
| 2010/0134627 A1* | 6/2010 | Yen | G06K 9/00771 348/159 |
| 2010/0222976 A1* | 9/2010 | Haug | B60K 28/04 701/70 |
| 2011/0090047 A1 | 4/2011 | Patel | |
| 2011/0307123 A1* | 12/2011 | Abe | G07C 9/00182 701/2 |
| 2012/0303392 A1* | 11/2012 | Depura | H04W 52/0258 705/4 |
| 2013/0027208 A1 | 1/2013 | Tao | |
| 2013/0070043 A1* | 3/2013 | Geva | B60K 28/066 348/14.02 |
| 2013/0204153 A1* | 8/2013 | Buzhardt | A61B 5/0476 600/544 |
| 2013/0297099 A1 | 11/2013 | Rovik | |
| 2014/0039934 A1* | 2/2014 | Rivera | G06Q 40/08 705/4 |
| 2014/0089101 A1* | 3/2014 | Meller | G06Q 40/08 705/14.66 |
| 2014/0293053 A1* | 10/2014 | Chuang | A61B 5/6893 348/148 |
| 2014/0309864 A1 | 10/2014 | Ricci | |
| 2015/0019266 A1* | 1/2015 | Stempora | G06Q 40/08 705/4 |
| 2015/0025917 A1* | 1/2015 | Stempora | G06Q 40/08 705/4 |
| 2015/0127215 A1 | 5/2015 | Chatterjee | |
| 2015/0140954 A1* | 5/2015 | Maier | H04W 4/22 455/404.2 |
| 2015/0160019 A1 | 6/2015 | Biswal et al. | |
| 2015/0197205 A1 | 7/2015 | Xiong et al. | |
| 2015/0263886 A1* | 9/2015 | Wang | H04L 41/08 370/254 |
| 2015/0328985 A1* | 11/2015 | Kim | H04N 5/23299 180/272 |
| 2015/0334545 A1* | 11/2015 | Maier | H04W 4/005 455/404.2 |
| 2016/0001781 A1 | 1/2016 | Fung et al. | |
| 2016/0016473 A1* | 1/2016 | Van Wiemeersch | B60W 50/12 701/36 |
| 2016/0042637 A1* | 2/2016 | Cahill | G08B 25/10 701/3 |
| 2016/0180144 A1* | 6/2016 | Tatourian | G01C 21/00 382/104 |
| 2016/0272214 A1 | 9/2016 | Sham | |
| 2016/0330601 A1* | 11/2016 | Srivastava | H04W 4/22 |
| 2017/0011562 A1* | 1/2017 | Hodges | G07C 5/008 |
| 2017/0174158 A1 | 6/2017 | Ding | |
| 2017/0305349 A1 | 10/2017 | Naboulsi | |
| 2017/0355377 A1* | 12/2017 | Vijaya Kumar | B60W 40/08 |

OTHER PUBLICATIONS

Lu et al., "A New Stochastic Model to Interpret Heart Rate Variability." Proceedings on the 25th Annual International Conference of the IEEE EMBS. Sep. 17-21, 2003.
Pogue, David, iPhone: The Missing Manual, Nov. 17, 2014, O'Reilly Media, 8th Edition, Chapter 2 and Chapter 4, 34 pages. Retrieved from http://techbus.safaribooksonline.com/print?xmlid=9781491947982%Fch01.
U.S. Appl. No. 14/977,627, filed Dec. 21, 2015 Non-Final Rejection dated Apr. 7, 2016, all pages.
U.S. Appl. No. 14/977,627, filed Dec. 21, 2015 Final Rejection dated Oct. 20, 2016, all pages.
U.S. Appl. No. 14/977,627, filed Dec. 21, 2015 Notice of Allowance dated Feb. 28, 2017, all pages.
U.S. Appl. No. 62/272,706, filed Dec. 30, 2015, Inventor: Wellen Sham.
European Search Report for EP17179153 dated Oct. 19, 2017, all pages.
U.S. Appl. No. 15/675,108, filed Aug. 11, 2017 Non-Final Rejection dated Nov. 30, 2017, all pages.
U.S. Appl. No. 15/675,142, filed Aug. 11, 2017 Non-Final Rejection dated Dec. 6, 2017, all pages.

* cited by examiner

SAFETY DRIVING SYSTEM

BACKGROUND

The present disclosure relates to vehicle monitoring technology, and more particularly to methods for increasing vehicle safety by monitoring a vehicle whose operator has been detected to have an abnormal physical condition.

A driver's abnormal physical condition could lead to unsafe driving causing an accident. A driver may suffer a debilitating medical condition and may lose his/her consciousness temporarily and drive erratically to cause a havoc on the road. A person suffering a seizure can lose control of his/her body, change the way he/she acts and senses things, or makes him/her unconscious suddenly. If a driver suffers a seizure while driving, the driver could lose control of the car and cause a crash.

Epilepsy is another a common neurological disorder that can involve loss of consciousness, convulsive movements or other motor activity, sensory phenomena, or behavioral abnormalities. Because of the potential for rapid incapacitation of the driver, and of the unpredictability of the illness, epilepsy place the individual at risk for motor vehicle crashes if the seizure occurs while driving. Statistics has shown people with epilepsy are more likely to be involved in a traffic accident than people who do not have the condition, although reports range from minimally more likely up to seven times more likely.

Sleep disorders are also responsible for many motor vehicle crashes. For example, sleep apnea is a common disorder affecting a substantial portion of the population. The risk is obvious when someone falls asleep at the wheel. Drivers who are sleepy have delayed reactions and make bad decisions. Not only are they putting themselves in danger, but they are a risk to everyone else on the road.

Crashes due to cardio vascular disease while driving represent one possible tragic outcome for individuals with coronary heart disease, and is a source of potential danger to other road users. Sudden cardiac death as a result of an arrhythmia is the most feared complication amongst drivers with existing CVD conditions. Even a benign arrhythmia, for example supraventricular tachycardia (SVT), may cause syncope, and hence incapacitate a driver.

A number of prescription and over-the-counter medications can negatively affect a person's cognitive performance. User of certain medications, such as antidepressants, antihistamines, benzodiazepines, or other medication can impair one's driving performance, especially the elderly drivers. For example, most common antidepressants comprise sedatives that may impair one's psychomotor performance. Significant impairments in psychomotor and driving performance have been noted by various studies.

In most places, driving authorities require a driver with a medical condition that can lead to unsafe driving to follow physical checkups regularly to ensure the driver is still fit to drive. Standards and regulations have been set in many cases to prohibit a driver with certain medical condition from driving either temporarily or permanently. However it is common for people with such medical conditions to hide their condition from authorities in order not to be denied a driver's license. Even with the drivers that are known to have medical conditions that can impair their driving performance, risks still exist. For example, such a driver may simply ignore their ailments and choose to drive, and thus potentially put him/her-self and others on the road at risk. Even with a responsible driver, that he or she takes all the necessarily steps to ensure his/her fitness to driver, it is not uncommon such a driver forgets to take these steps occasionally. Data has shown most medical causes of road accidents occur in drivers who are already known to have pre-existing disease.

Accordingly, there is a need to have a driving apparatus that are equipped to detect abnormal physical conditions of a driver while driving, and to notify relevant entities to address risks associated the abnormal physical conditions.

SUMMARY

Embodiments are provided for monitoring physical conditions of an operator of a driving apparatus to improve transportation safety. The driving apparatus can be equipped with one or more sensing devices to acquire signals indicating various physical conditions of the operator. The sensing devices may include a EKG sensing device, a EEG sensing device, a body temperature sensing device, a BAC sensing device, a photography device and/or any other sensing devices. The signals acquired by the various sensing devices can be processed and analyzed for detecting whether one or more abnormal physical conditions of the operator have occurred. The one or more physical conditions can include heart activities, EEG activities, body temperature, blood alcohol level, eye movement and/or any other physical conditions of the operator. A status indicating an abnormal physical condition having been detected can be generated in response to an abnormal physical condition of the operator having been detected.

In certain embodiments, a status indicating that a particular sensing device is disconnected from the operator (a "disconnect status") can be generated when signals are not received from the particular sensing device and the driving apparatus is being operated by the operator. For example, such a status can be generated when the driving apparatus is being operated by the operator but no EEG signals are acquired from the operator by the EEG sensing device.

In certain embodiments, a control center is provided to facilitate monitoring physical conditions of an operator of a driving apparatus to improve transportation safety. The control center can comprise one or more servers and one or more human operators. The one or more servers can be configured to manage user accounts for individual operators associated with different driving apparatuses. The one or more servers can be configured to receive a status indicating whether an abnormal physical condition of a particular operator of a driving apparatus has been detected. The one or more servers can be configured to receive information regarding the particular operator and/or the driving apparatus from the driving apparatus. The one or more servers can be configured to generate an alert in response to the status indicating an abnormal physical condition of the operator having been detected. In certain embodiments, the one or more servers can be configured to generate an alert in response to the status indicating a disconnect status having been detected for the driving apparatus operated by the operator. In certain embodiments, the one or more servers can be configured to determine a risk level based on the information regarding the abnormal physical condition received for the operator, information identifying the operator, and/or any other information. In certain embodiments, the one or more servers can be configured to generate notifications based on the determined risk level. The notifications can include a notification to a human operator in the control center, a notification to a healthcare facility, a law enforcement agency, an emergency contact for the operator, an insurance company of the operator, and/or any other entities.

In certain embodiments, a drone is provided to facilitating monitoring physical conditions of an operator of a driving apparatus to improve transportation safety. The drone can be equipped with a wireless transceiver configured to receive location information along with identification information from the driving apparatus. After the driving apparatus having been identified to be associated with certain level of risk as determined by the control center, the one or more servers in the control center can be configured to instruct the drone to track the driving apparatus, and transmit location information regarding the driving apparatus from time to time.

Other objects and advantages of the invention will be apparent to those skilled in the art based on the following drawings and detailed description.

BRIEF DESCRIPTION OF THE DRAWINGS

The accompanying drawings, which are included to provide a further understanding of the invention, are incorporated in and constitute a part of this specification, illustrate embodiments of the invention and together with the detailed description serve to explain the principles of the invention. No attempt is made to show structural details of the invention in more detail than may be necessary for a fundamental understanding of the invention and various ways in which it may be practiced.

In the appended figures, similar components and/or features may have the same numerical reference label. Further, various components of the same type may be distinguished by following the reference label by a letter that distinguishes among the similar components and/or features. If only the first numerical reference label is used in the specification, the description is applicable to any one of the similar components and/or features having the same first numerical reference label irrespective of the letter suffix.

DETAILED DESCRIPTION OF THE INVENTION

Various specific embodiments of the present disclosure will be described below with reference to the accompanying drawings constituting a part of this specification. It should be understood that, although structural parts and components of various examples of the present disclosure are described by using terms expressing directions, e.g., "front", "back", "upper", "lower", "left", "right" and the like in the present disclosure, these terms are merely used for the purpose of convenient description and are determined on the basis of exemplary directions displayed in the accompanying drawings. Since the embodiments disclosed by the present disclosure may be set according to different directions, these terms expressing directions are merely used for describing rather than limiting. Under possible conditions, identical or similar reference numbers used in the present disclosure indicate identical components.

Figure 1:
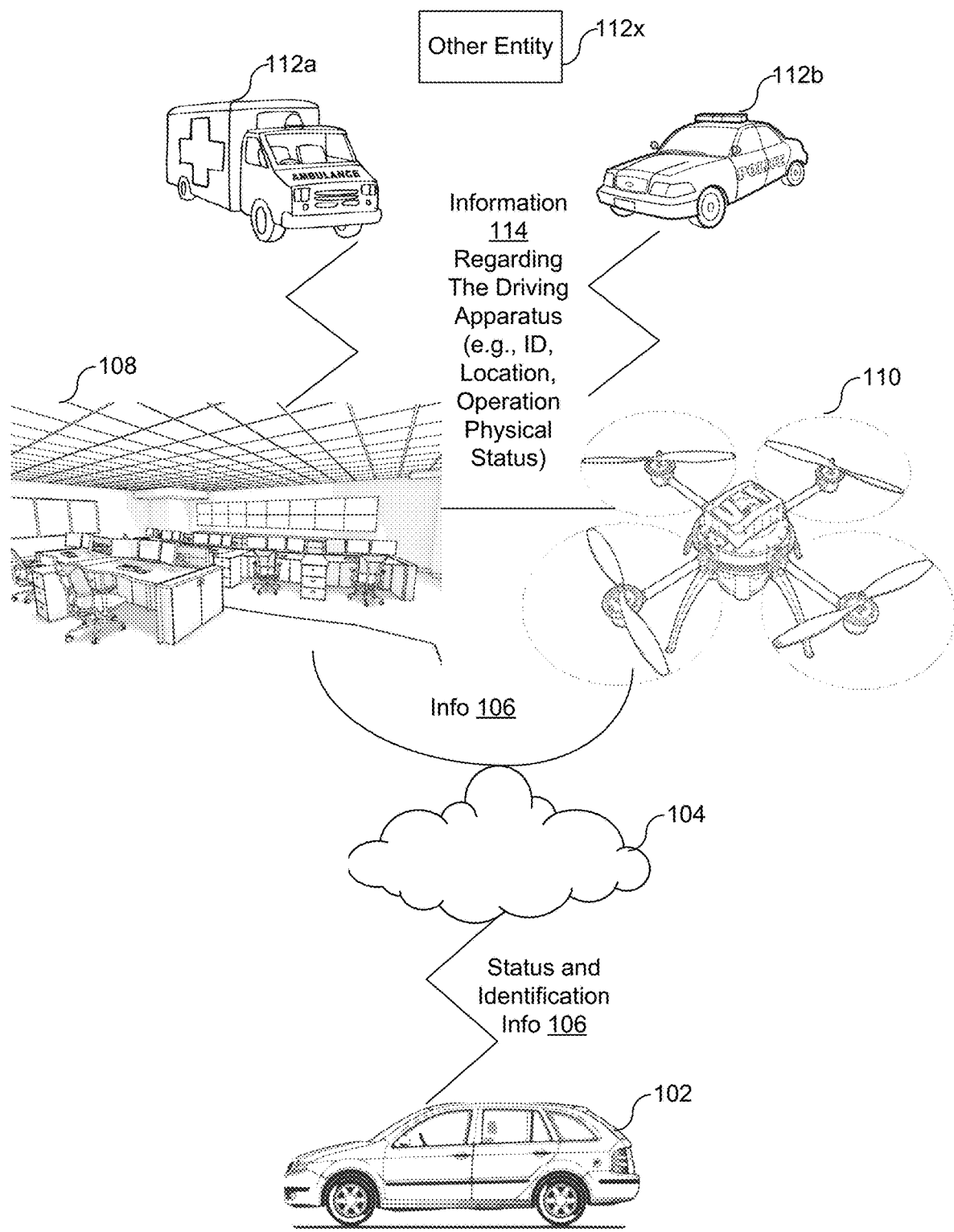
FIG. 1 generally illustrates an infrastructure for facilitating monitoring abnormal physical condition of an operator of a driving apparatus to improve safety in accordance with the disclosure.

FIG. 1 generally illustrates an infrastructure for facilitating monitoring abnormal physical condition of an operator of a driving apparatus 102 to improve safety in accordance with the disclosure. The driving apparatus 102 may include any driving apparatus that moves in distance. Examples of driving apparatus 102 may include a vehicle such as a car, a bus, a train, a truck, a tram, or any other type of vehicle; may include a vessel such as a boat, a ship, a barge, a ferry or any other type of watercraft; may include an aircraft such as an airplane, a spaceship, or any other type of aircraft; or may include any other transportation apparatus. In one example, the driving apparatus 102 is an electrical automobile. As shown, the driving apparatus 102 can generate information 106 from time to time. The information 106 can include a status indicating an abnormal physical condition ("abnormal condition status") having been detected for the operator of the driving apparatus 102, a status indicating that a particular sensing device is disconnected from the operator (a "disconnect status"), and/or any other status information regarding the operator of the driving apparatus 102. The information 106 can include identification information regarding the operator of the driving apparatus 102, and/or the apparatus 102. The abnormal condition status generated by driving apparatus 102 can indicate abnormal EKG activities, an EEG pattern, an abnormal body temperature, an abnormal BAC level, an abnormal eye movement and/or any other abnormal physical conditions of the operator of the driving apparatus having been detected.

As shown, the information 106 can be transmitted from driving apparatus 102 to a control center 108 and/or a drone 110 via a network 104. The network 104 can employ a wireless transmission technology such as ultra high frequency radio, cellular, WIFI, bluetooth, infrad, laser, and/or any other wireless transmission technology. Information 106 can be transmitted through network 104 to the control center 108. The control center 108 can house one or more servers. The one or more servers in the control center 108 can be configured to receive information 106. The one or more servers in the control center 108 can be configured to generate a notification in response to the status indicating an abnormal physical condition of the operator having been detected as indicated by information 106. In certain embodiments, the one or more servers in the control center 108 can be configured to generate a notification in response to the status indicating a disconnect status having been detected for the driving apparatus 102 as indicated by information 106. In certain embodiments, the one or more servers in the control center 108 can be configured to determine a risk level based on the information 106, and/or any other information. In certain embodiments, the one or more server in the control center 108 can be configured to generate notifications based on the determined risk level. The notifications can include a notification to a human operator in the control center 108, a notification to a healthcare facility 112a, a law enforcement agency 112b, an emergency contact for the operator of driving apparatus 102, an insurance agency, and/or any other entities. The notification can include identification information 114 regarding the operator and/or the driving apparatus 102.

In certain embodiments, one or more of a drone 110 can be provided to facilitate monitoring the driving apparatus 102. The drone 110 can be equipped with a wireless transceiver configured to communicate with the driving apparatus 102, the control center 108, and/or any other entities. In certain embodiments, the drone 110 can be configured to receive information 114 regarding the operator and/or the driving apparatus 102. The drone 110 can be configured to track the driving apparatus 102 that is identified through information 114. For example, the drone 110 may be configured to communicate with the driving apparatus 102 through a pre-assigned high frequency radio channel while the driving apparatus 102 is in an area monitored by the drone 110. The drone 110 can be configured to obtain location information regarding the driving apparatus 102 from time to time through the pre-assigned high frequency radio channel. The drone 110 can transmit the location information regarding the driving apparatus 102 back to the control center 108, which can update various entities such as health care facility 112b, law enforcement agency 112b and/or any other entities, with the updated location information regarding the driving apparatus 102. In this way, drone 110 can be used to provide positioning service to track the driving apparatus 102.

Figure 2:
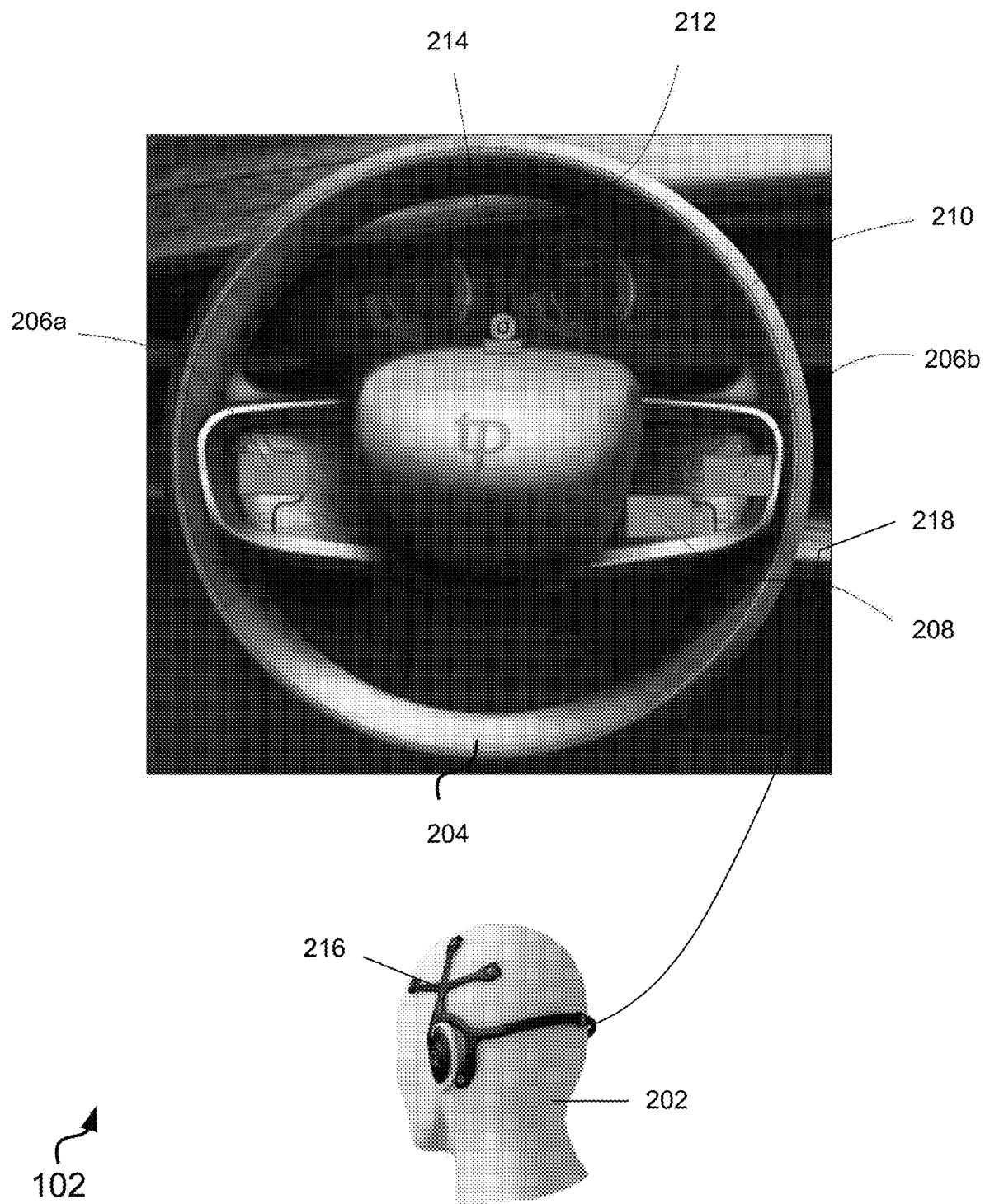
FIG. 2 illustrates certain sensing devices that can be placed within driving apparatus shown in FIG. 1.

With the infrastructure for facilitating monitoring the driving apparatus 102 to improve safety having been generally described, attention is now directed to FIG. 2. FIG. 2 illustrates some sensing devices that can be placed within driving apparatus 102 for generating an abnormal condition status, and/or a disconnect status as described above. As shown, in certain embodiments, as in this embodiment, the driving apparatus 102 can be operated by an operator 202 through a steering wheel 204. The driving apparatus 102 can comprise one or more sensing devices arranged at different positions on the steering wheel 204 of the driving apparatus 102. However, the arrangement of the sensing devices in the driving apparatus 102 illustrated in FIG. 2 is not intended to be limiting. The sensing devices may be arranged at various locations throughout the driving apparatus 102 other than around the steering wheel 204. In U.S. patent application Ser. No. 62/272,706, filed Dec. 30, 2015 and entitled "METHOD FOR RECOGNIZING VEHICLE DRIVER AND DETERMINING WHETHER DRIVER CAN START VEHICLE", various sensing devices and methods thereof are provided. U.S. patent application Ser. No. 62/272,706 is incorporated by reference herein.

As shown in this example, the sensing devices may include electrocardiogram (EKG) sensing devices 206a and 206b arranged on the left side and the right side of the steering wheel 204, a fingerprint detection device 208, an alcohol detection device 210, a body temperature detection device 212 in the middle of the steering wheel 204, and a photography device 214, a EEG sensing device 216, an EEG signal processing device 218 and/or any other sensing devices.

The EKG sensing devices 206a and 206b can be configured to acquire EKG signals reflecting heart activities of operator 202. The EKG sensing devices 206a and 206b can be activated when the operator 202's hands are laid on the two sides of the steering wheel 204. The EKG signals acquired by the EKG sensing devices 206a and 206b can indicate magnitudes of heart electrical potentials of operator 202. The measured heart potentials can be recorded over a period of time, for example 10 seconds. The overall magnitude and direction of heart's electrical depolarization can then be captured and analyzed to extract different cardiac characteristics of operator 202, including P, Q, R, S and T waves.

The fingerprint sensing device 208 can be configured to acquire a fingerprint image of operator 202. The fingerprint image can be captured through any one of a wide number of available fingerprint scanning technologies that may be employed by fingerprint sensing device 208. For example, fingerprint sensing device 208 can include an optical sensor, a capacitive sensor, an ultrasound sensor, or a thermal sensor, among others. In some embodiments, fingerprint sensing device 208 may be a capacitive sensor that determines each pixel value of an image based on the capacitance measured at each pixel location, which varies due to the different dielectric constants of skin ridges compared to a valleys. In some embodiments, fingerprint sensing device 208 may employ a high frequency ultrasound or optical sensor that receives a varying signal based on the change in light reflectance related to the skin ridges. In some embodiments, fingerprint sensing device 208 can include a thermal scanner that measures the difference in temperature of different pixel areas, with high temperature areas corresponding to skin ridges and low temperature areas corresponding to valleys.

In certain embodiments, the signal that is captured by fingerprint detection device 103 can be an image file. The image file may be compressed or uncompressed, and may be any one of several digital image file types, such as TIFF, JPEG, GIF, PNG, BMP, etc. In some embodiments, the image file may not be a traditional image file type, but may be a data representation of fingerprint topography. For example, while a fingerprint usually appears as a series of dark lines that represent ridges of the skin, the image file may be an integer representing the number of ridges of the skin. Furthermore, the image file may be an integer representing the number of crossovers, ridge bifurcations, ridge endings, islands, or pores. Furthermore, the image file may be any digital representation of any feature of a fingerprint.

The alcohol detection device 210 can be configured to acquire samples of breathing gas provided by operator 202 to estimate the operator 202's blood alcohol content (BAC) level. In certain embodiments, a fuel cell can be arranged in or with the alcohol detection device 210. In some embodiments, the fuel cell can convert alcohol in the breathing gas of the operator 202 into an electrical signal of which the quantity of electricity is directly proportional to the alcohol content to determine the degree of intoxication of the driver.

In certain embodiments, the alcohol detection device 210 can be configured to require the operator 202 to give a breathing gas sample before operator 202 can operate the driving apparatus 102. For example, the finger detection device 208 can be configured to obtain an identity of the operator, and the obtained identity of the operator may indicate that the operator has a history of driving under influence. In that case, the alcohol detection device 210 can require the operator 202 to give a breathing gas sample, analyze the sample to extract a level of BAC from the sample, compare the level of the BAC with a predetermined threshold indicating a maximum of legally permissible level of BAC, determine whether the measured BAC level of operator 202 has exceeded that threshold, and transmit the result of the determination to a processing device for further processing. In certain embodiments, the alcohol detection device 210 can include a breathalyzer in which the driver may breathe directly into to yield a BAC estimate.

The body temperature detection device 212 can be configured to acquire a body temperature signal of operator 202 once in a time period, for example once every minute. The body temperature signal can indicate a reading of a body temperature of operator 202. The body temperature detection device 212 can be configured to determine whether the acquired reading of the body temperature of operator 202 has exceeded a predetermined maximum body temperature threshold or has dropped below a predetermined minimum body temperature threshold. The body temperature of operator 202 can be configured to generate information to indicate a determination of such have been made. In certain embodiments, an infrared thermometer and a detector can be arranged in or with the body temperature detection device 212. In some embodiments, the infrared thermometer can collect human infrared energy and gathers the infrared energy in the detector. The detector may then convert the infrared energy into an electrical signal.

The photography device 214 can include a camera and can be configured to capture an image of operator 202's face from time to time and analyze the captured image. For example, the photography device 214 can be configured to capture an image of operator 202's face once every 10 seconds. The analysis performed by photography device 214 can include image recognition to identify operator 202. In certain embodiments, the analysis performed by photography device 214 can include analysis for detecting an eye movement of the operator 202 to determine whether operator 202 is sleeping or is drowsy.

The EEG device 216 can be configured to acquire signals indicating EEG activities of operator 202. As shown the EEG device 216 can be a wearable device that can be worn by operator 202 on the head. The EEG device 216 may include one or more electrodes, each of which can be connected to on input of a differential amplifier. The electrodes can acquire signals indicating electrical potentials generated by neurons of operator 202. The amplifiers can amplify the voltage to generate EEG signals indicating brain activities of operator 202. In certain embodiments, as in this example, the EEG device 216 can be operatively connected to an EEG processing device 218. In those embodiments, the EEG signals acquired by the EEG device 216 can be processed and analyzed to determine whether the EEG activities of operator 202 is abnormal.

Figure 3:
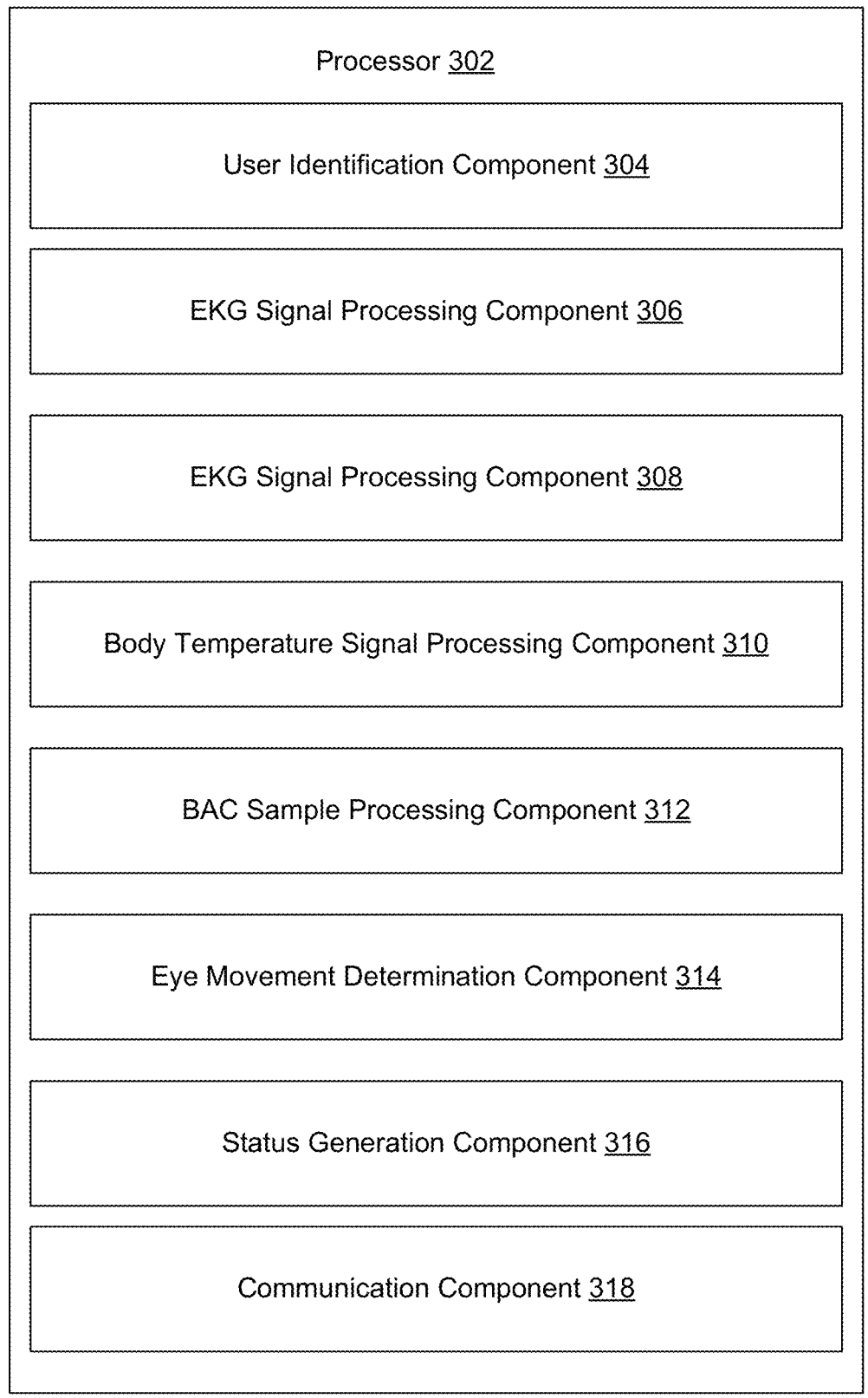
FIG. 3 illustrates an exemplary system configured to facilitate monitoring physical conditions of an operator of a driving apparatus to improve safety in accordance with the disclosure.

FIG. 3 illustrates an exemplary system 300 configured to facilitate monitoring physical conditions of an operator of a driving apparatus 102 to improve safety in accordance with the disclosure. As shown, system 300 can include one or more of a processor 302 configured to implement computer program components. The computer program components can include a user identification component 304, a EKG signal processing component 306, a EEG signal processing component 308, a body temperature signal processing component 310, an eye movement determination component 314, a status generation component 316, a communication component 318, and/or any other components.

The user identification component 304 can be configured to identify the operator 202. The identification of the operator 202 by the user identification component 304 can be made based on the fingerprint image acquired by the fingerprint detection device 208, the image of operator 202's face captured by the photography device 214, and/or any other identification information regarding operator 202. For example, the identification by the user identification component 304 may involve analyzing features in the fingerprint image and/or in the facial image of the operator 202, and compared the obtained features with features of registered operators. Upon a match, the user identification component 304 can be configured to obtain a user ID of the identified operator 202.

The EKG signal processing component 306 can be configured to receive EKG signals generated by the EKG sensing device 206; and to analyze the EKG signals. The analysis of the EKG signals by the EKG signal processing component 306 can include acquiring the user ID determined by the user identification component 304, retrieving a predetermined EKG patterns for the identified operator 202 using the user ID, comparing the EKG signals with the retrieved EKG pattern, and/or any other operations. In the case when an abnormal EKG pattern is determined for the identified operator 202, a control signal can be generated to instruct the status generation component 316 to generate a status accordingly.

In certain embodiments, the EKG signal processing component 306 can be configured to generate a control signal after not receiving the EKG signals from the EKG sensing device 206 for a predetermined period of time, for example 20 seconds. Such a control signal can be transmitted to the status generation component 316 for generating a status indicating that no EKG signals have been detected from the operator 202 for more than 20 seconds. Such a status can be used to determine whether the operator 202 has suffered a sudden death or simply is disconnected from the EKG sensing device 206.

The EEG signal processing component 308 can be configured to receive EEG signals generated by the EEG device 216; and to analyze the EEG signals. The analysis of the EEG signals by the EEG signal processing component 308 can include acquiring the user ID determined by the user identification component 304, retrieving a predetermined EEG patterns for the identified operator 202 using the user ID, comparing the EEG signals with the retrieved EEG pattern, and/or any other operations. In the case when an abnormal EEG pattern is determined for the identified operator 202, a control signal can be generated to instruct the status generation component 316 to generate a status accordingly.

In certain embodiments, the EEG signal processing component 308 can be configured to generate a control signal after not receiving the EEG signals from the EEG device 216 for a predetermined period of time, for example 20 seconds. Such a control signal can be transmitted to the status generation component 316 for generating a disconnect status indicating that no EEG signals have been detected from the operator 202 for more than 20 seconds. Such a status can be used to determine whether the operator 202 has suffered an sudden death or simply is disconnected from the EEG device 216.

The body temperature signal processing component 310 can be configured to receive body temperature signals generated by the body temperature sensing device 212; and to analyze the body temperature signals. The analysis of the body temperature signals by the body temperature signal processing component 310 can include acquiring the user ID determined by the user identification component 304, retrieving a predetermined minimum and/or maximum normal body temperature thresholds for the identified operator 202 using the user ID, comparing the body temperature signals with the retrieved thresholds, and/or any other operations. In the case when an abnormal body temperature, i.e., the obtained body temperature of operator 202 is above the maximum threshold or is below the minimum threshold, is detected for the identified operator 202, a control signal can be generated to instruct the status generation component 316 to generate a status accordingly.

The BAC sample processing component 312 can be configured to receive BAC level signal generated by the BAC sensing device 214; and to analyze the received BAC level. The analysis of the BAC level by the BAC sample processing component 312 can include acquiring the user ID determined by the user identification component 304, retrieving a predetermined normal BAC level thresholds for the identified operator 202 using the user ID, comparing the BAC level with the retrieved thresholds, and/or any other operations. In the case when an BAC level, i.e., the obtained BAC level of operator 202 is above a maximum threshold, is detected for the identified operator 202, a control signal can be generated to instruct the status generation component 316 to generate a status accordingly.

The eye movement determination component 314 can be configured to determine an eye movement of the operator 202 based on a facial image captured by the photography device 214. The determination by the eye movement determination component 314 may involve determining a position of an eyeball or eyeballs of the operator 202 in the received facial image. Position changes to the eyeball(s) between two images captured in sequence can be determined based on the position of the eye(s) in each image. An eye movement of the eye(s) of operator 202 can be estimated based on the determined position changes. The eye movement determination component 314 can be configured to determine whether the operator 202 is asleep or drowsy based on the determined eye movement. For example, if the position of the eyeball(s) of the operator cannot be detected for a time period, the operator 202 can be determined to be asleep because it is likely the operator 202 has closed his/her eyes.

The status generation component 316 can be configured to generate one or more statuses indicating various abnormal physical conditions have been detected for operator 202, and/or indicating a sensing device in the driving apparatus has been disconnected from the operator 202. The statuses generated by the status generation component 316 may include a status indicating that abnormal EKG activities have been detected, a status indicating that abnormal EEG patterns have been detected, a status indicating that an abnormal body temperature has been detected, a status indicating that an abnormal BAC level has been detected, a status indicating that an abnormal eye movement has been detected, and/or any other statuses. In certain embodiments, the status generated by the status generation component 316 can include a status indicating the EKG sensing device is disconnected from the operator 202, a status indicating EKG signals have not been received for the operator 202 for more than a predetermined period of time, a status indicating the EEG sensing device is disconnected from the operator 202, a status indicating EEG signals have not been received for the operator 202 for more than a predetermined period of time, and/or any other statues.

The communication component 318 can be configured to communicate the status(es) generated by the status generation component 316, identification information regarding the operator 202 and/or driving apparatus 102, and/or any other information to control center 108, drone 110, and/or any other entities. The communication component 318 can be configured to communicating such information via the network 104.

It should be understood the above-described functionalities attributed to system 300 can be implemented within the driving apparatus 102. For example, driving apparatus 102 can be equipped with system 300 to process various signals acquired by the sensing devices shown in FIG. 2. However, this is not necessarily the only case. In certain embodiment, part of or the entire functionalities attributed to system 300 herein can be implemented at the control center 108. For example, the control center 108 may comprise a server that can be configured to perform part of the operations provided by system 300 as described above.

Figure 4:
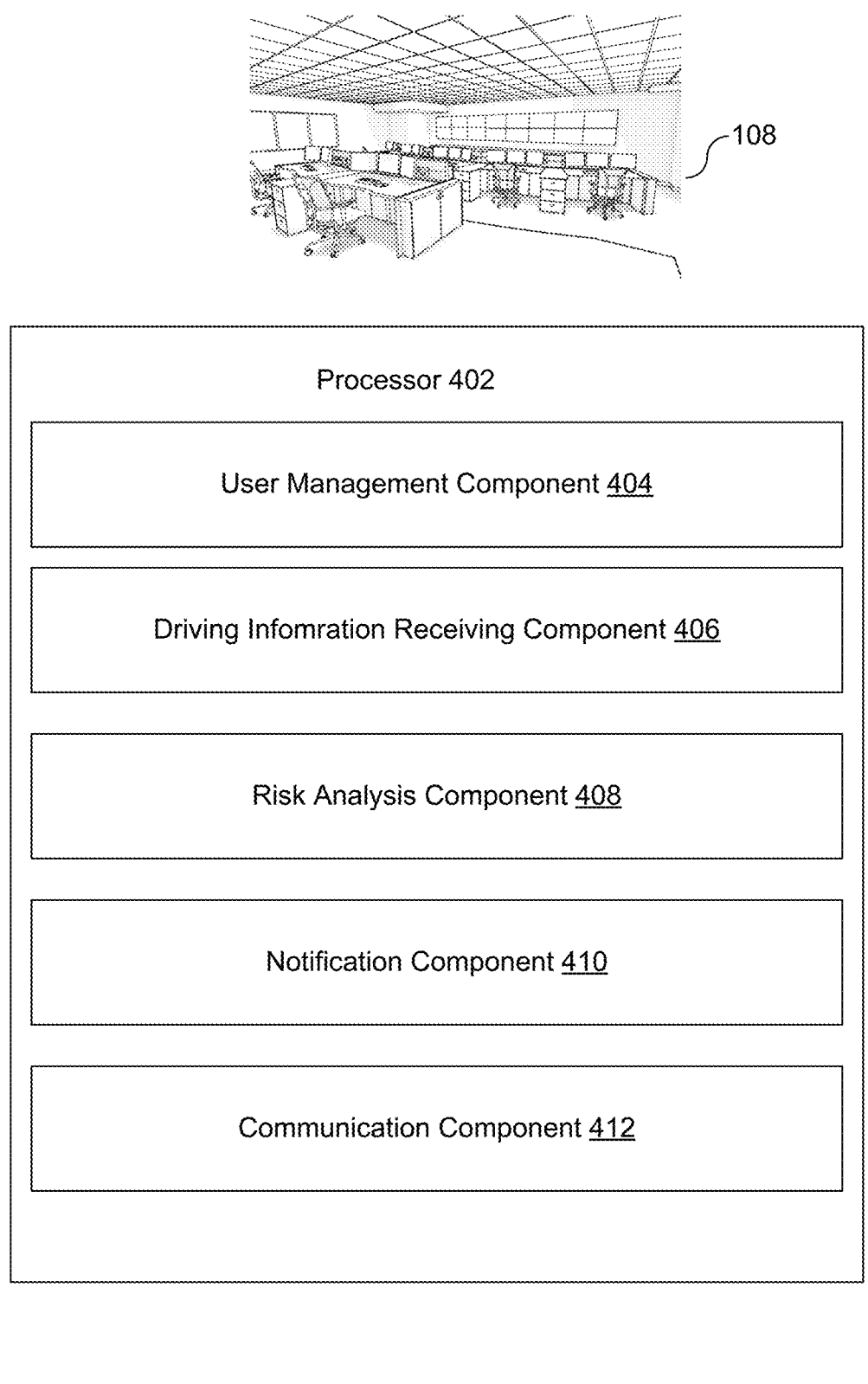
FIG. 4 illustrates an example of a server that can be included in a control center shown in FIG. 1 to facilitate monitoring physical conditions of operators of driving apparatus shown in FIG. 1 in accordance with the disclosure.

Attention is now directed to FIG. 4. FIG. 4 illustrates a server 400 that can be included in the control center 108 to facilitate monitoring physical conditions of operators of driving apparatus 102 in accordance with the disclosure. As shown, the server 400 can include a user management component 404, a driving information receiving component 406, a risk analysis component 408, a notification component 410, a communication component 412, and/or any other components. The user management component 404 can be configured to manage user accounts for individual users managed by control center 108 or users of a provider affiliated with control center 108. The user accounts managed by the user management component 404 can include a first user account for a first user. The first user may be associated with one or more of a driving apparatus, such as driving apparatus 102. The first user account may include first user information regarding an identity of the first user, a medical history of the first user, a driving history of the first user, an insurance record associated with the first user, a healthcare record associated with the first user, a criminal history of the first user, one or more emergency contacts for the first user and/any other information regarding the first user. For example, the identity of the first user may include a name of the first user, an address of the first user, an age of the first user, a language spoken by the first user, and/or any other identity information regarding the first user. As another example, the medical history of the first user can include one or more diagnoses for the first user, one or more hospital/office/clinic visits by the first user, one or more medication currently being taken or having been taken by the first user, and/or any other information regarding the first user.

The driving information receiving component 406 can be configured to receive driving information from individual driving apparatuses 102. For example, the driving information receiving component 406 can receive such information via the communication component 412. The driving information received by the driving information receiving component 406 can include information 106 received from driving apparatus 102. As described above, the information 106 can include various status information regarding physical conditions of operator 202 of driving apparatus 102. For example, the operator 202 can be the first user. In that example, the status information received by driving information receiving component 406 can include status(es) regarding one or more physical condition of the first user. For example, the statuses may include a status indicating an abnormal EKG, EEG, body temperature, eye movement of first user, and/or any other abnormal physical conditions of the first user. In certain embodiments, the information for the first user as received by the driving information receiving component 406 can include identification information regarding the first user and/or the driving apparatus. The identification information regarding the first user can include a userID of the first user, a name of the first user, a telephone number of the first user, and/or any other identification information regarding the first user. The identification information regarding the driving apparatus 102 can include an apparatus identification number, a model, year and make of driving apparatus 102, a color of driving apparatus 102, and/or any information regarding the driving apparatus 102.

In certain embodiments, "raw" data of signals acquired by various sensing devices can be received by server 400 via the driving information receiving component 406. In those embodiments, the driving information receiving component 406 can be configured to store the raw data in a data store associated with server 400. The raw data may include unprocessed signals acquired by the various sensing devices described in FIG. 2. Such data can be used by server for further processing.

The risk analysis component 408 can be configured to determine a level of risk posed by a driving apparatus 102. The determination of the risk level by the risk analysis component 408 can be based on the driving information received by the driving information receiving component 406. For example, the driving information received by the driving information receiving component 406 may include status information indicating that the operator 202 of driving apparatus 102 has abnormal EEG activities. In response to this information having been received, the risk analysis component 408 can be configured to obtain a medical history of the operator 202 and to determine if operator 202 has suffered epilepsy or seizure in the past. If it is determined that operator 202 has suffered epilepsy or seizure in the past, a high risk level can be determined by the risk analysis component 408 to indicate the operator 202 operating driving apparatus 102 poses a high risk to public safety. As another example, the risk analysis component 408 can be configured to obtain a driving history and/or a criminal history of operator 202 in response to a status indicating an abnormal BAC level having been detected for operator 202. In that example, if the driving history of operator 202 indicating that the operator 202 had a history DUI records, a high risk level can be determined such that a law enforcement agency may be contacted by the control center 108 to stop driving apparatus 102. On the other hand, if the driving history of the operator does not indicate the operator 202 had any DUI record, a low risk level can be determined such that a human operator of the control center 108 can notified instead of law enforcement. In that case, the human operator can check the reading of BAC level of operator 202 to determine whether or not law enforcement should be notified. Other examples are contemplated.

The notification component 410 can be configured to generate a notification informing one or more abnormal physical conditions having been detected for a particular operator 202 that is operating a driving apparatus 102. The notification can include information identifying the operator such as a user ID or a name of operator 202. The notification can include information regarding driving apparatus 102, such as apparatus identification number, a license plate number, a current location of driving apparatus 102, a direction the driving apparatus 102 is traveling in, a speed the driving apparatus 102 is traveling at, and/or any other information regarding the driving apparatus 102. The notification can include a description of an abnormal physical condition has been detected for operator 202, a medical history of operator 202, a driving history of operator 202, a criminal history of operator 202, and/or any other information regarding the operator 202.

In certain embodiments, the notification component 410 can be configured to generate notifications based on risk level determined by the risk analysis component 408. A notification can be generated by the notification component 410 for a healthcare facility such as healthcare facility 112a when the risk level is determined be high and the operator 202 is indicated as suffering a seizure or a heart attack. The notification can request the healthcare facility 112a send an ambulance to the current location of the driving apparatus 102. As another example, a notification can be generated by the notification component 410 for a law enforcement agency when a risk level is determined to be high and the operator 202 is indicated as having abnormal BAC level. Still as another example, a notification can be generated by the notification component 410 for a human operator in the control center 108 when the risk level is determined be low and the operator 202 is indicated as having abnormal body temperature. In that case, the human operator can decide whether or not further actions are necessary.

The communication component 412 can be configured to communicate notifications to various entities such as the healthcare facility 102a, the law enforcement agency 102b, and/or any other entities 102x (e.g., an insurance company of operator 202, an emergency contact for operator 102). In certain embodiments, the communication component 412 can be configured to communicate with drone 110 for updated driving information regarding operator 106, and/or updated location information of driving apparatus 102.

Figure 5:
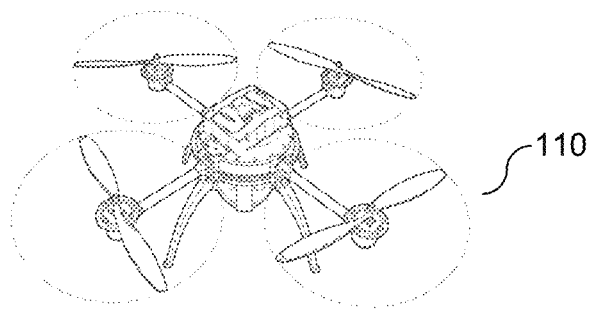
FIG. 5 illustrates an example of a system onboard drone shown in FIG. 1.
Figure 5:
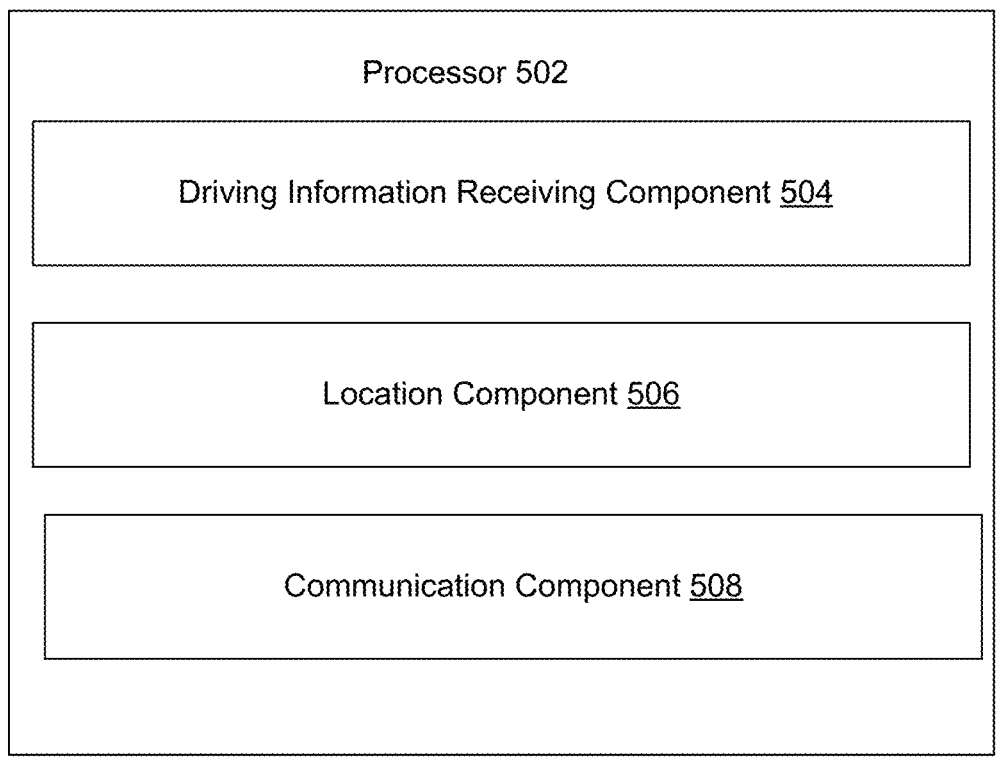

Attention is now directed FIG. 5, where a system 500 onboard drone 110 is illustrated. As shown, system 500 may include one or more of a processor 502 configured to implement computer program components. The computer program components can include a driving information receiving component 504, a location component 506, a communication component 508, and/or any other components. The driving information receiving component 504 can be configured to receive driving information from individual driving apparatuses 102 and as well as from one or more servers in one or more control centers 108. The driving information receiving component 406 can receive such information via the communication component 508. The driving information received by the driving information receiving component 504 can include information regarding the operator 202 of driving apparatus 102, such as an identification of driving apparatus 102 (e.g., license plate number or driving apparatus identification number), a current location of the driving apparatus 102, a speed at which the driving apparatus 102 is traveling at, a direction the driving apparatus 102 is traveling in, and/or any other information.

The location component 506 can be configured to obtain location information regarding the driving apparatus 102 identified by the driving information received by the driving information receiving component 504. The location information obtained by the location component 506 may be in the form of geo-location coordinates, or may be in the form of local coordinates in a coordinate system for an area monitored by drone 110. The location component 506 can be configured to obtain such location information regarding the identified driving apparatus 102 from time to time, for example once every minute. In implementations, drone 102 may be configured to enter a tracking mode to track a movement of driving apparatus 102 through a camera or radio transceiver on the done 110.

The communication component 508 can be configured to communicate the location information obtained by the location component 506 to the server 400 in the control center, to the healthcare facility 102a, to the law enforcement agency 102b, and/or to any other entities. The communication component 508 can be configured to communicate the location information regarding the identified driving apparatus 102 to such entities from time to time. For example, the communication component 508 can communicate the location information to the server 400 once every 10 seconds to update the current location of the driving apparatus 102.

Figure 6:
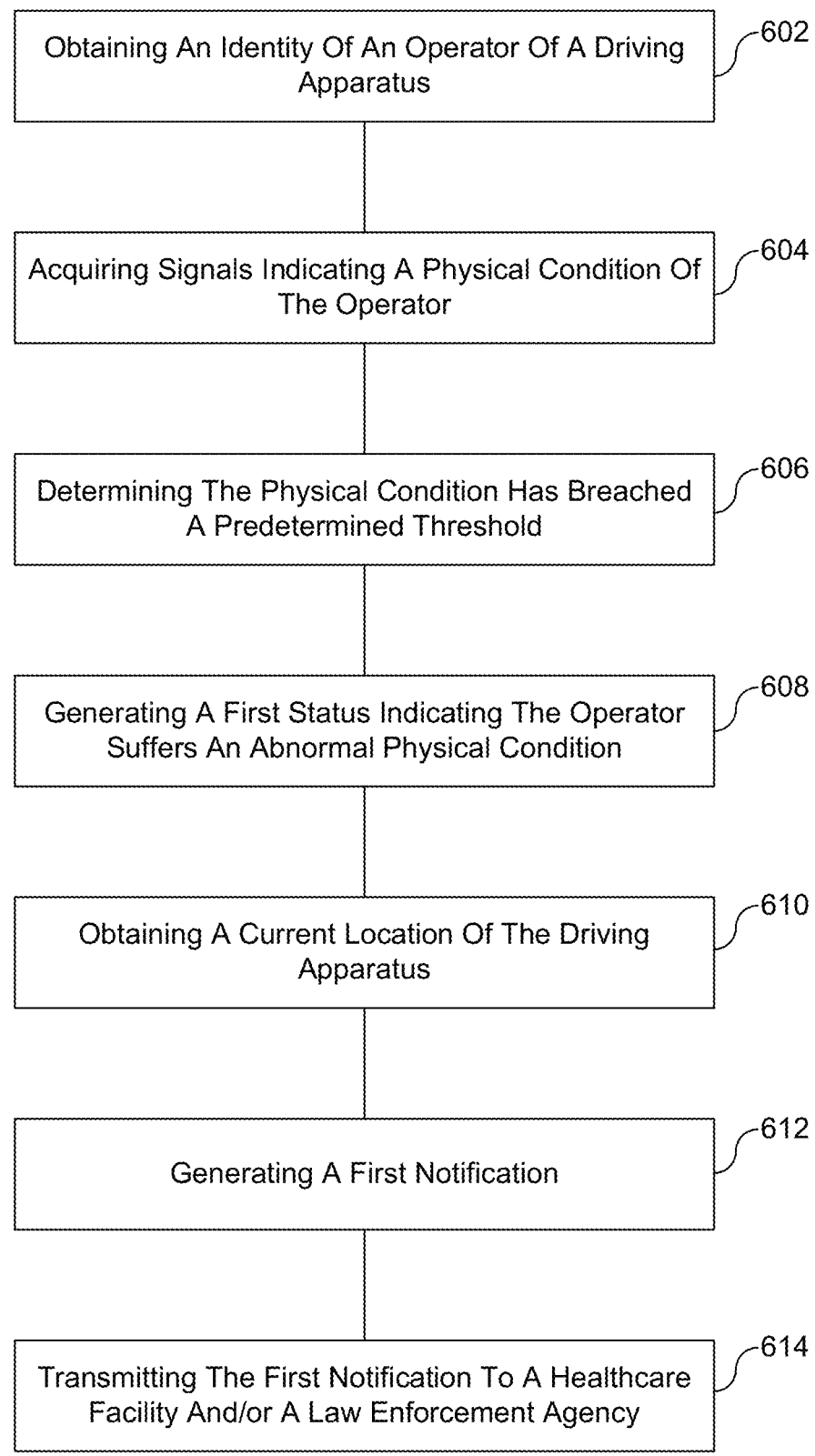
FIG. 6 illustrates one exemplary method for facilitating monitoring abnormal physical condition of an operator of a driving apparatus to improve safety.

FIG. 6 illustrates one exemplary method for facilitating monitoring abnormal physical condition of an operator of a driving apparatus to improve safety. The operations of method 600 presented below are intended to be illustrative. In some embodiments, method 600 may be accomplished with one or more additional operations not described and/or without one or more of the operations discussed. Additionally, the order in which the operations of method 600 are illustrated in FIG. 6 and described below is not intended to be limiting.

In some embodiments, method 600 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 600 in response to instructions stored electronically on an electronic storage medium. The one or more processing devices may include one or more devices configured through hardware, firmware, and/or software to be specifically designed for execution of one or more of the operations of method 600.

At 602, an identity of an operator of a driving apparatus can be obtained. In some implementations, operation 602 can be performed by a user identification component the same as or substantially similar to user identification component 304 described and illustrated herein.

At 604, signals indicating a physical condition of the operator can be acquired. The signals can be acquired from a sensing device. Examples of such a sensing device are illustrated in FIG. 2. The physical condition can include EKG activities, EEG activities, a body temperature, an eye movement, or any other physical condition of operator. In some implementations, operation 604 can be performed by a EKG signal processing component, EEG signal processing component, a body temperature signal processing component, a BAC sample processing component or an eye movement determination component the same as or substantially similar to the user identification component 304, the EKG signal processing component 306, the EEG signal processing component 308, the body temperature signal processing component 310, the BAC sample processing component 312, or the eye movement determination component 314 described and illustrated herein.

At 606, the physical condition as indicated by the signals acquired at 604 can be compared with a predetermined threshold and determined that it has breached the predetermined threshold. In some implementations, operation 606 can be performed by a EKG signal processing component, EEG signal processing component, a body temperature signal processing component, a BAC sample processing component or an eye movement determination component the same as or substantially similar to the user identification component 304, the EKG signal processing component 306, the EEG signal processing component 308, the body temperature signal processing component 310, the BAC sample processing component 312, or the eye movement determination component 314 described and illustrated herein.

At 608, a first status indicating the operator suffers an abnormal physical condition can be generated in response to the determination made at 606. In some implementations, operation 608 can be performed by status generation component the same as or substantially similar to status generation component 316 described and illustrated herein.

At 610, a current location of the driving apparatus can be obtained. In some implementations, operation 610 can be performed by a driving information receiving component the same as or substantially similar to driving information receiving component 406 described and illustrated herein.

At 612, a first notification can be generated. The first notification can include information indicating the identity of the operator as obtained at 602, and the current location of the driving apparatus as obtained at 610. The first notification can include information describing the first user suffers the abnormal physical condition. In some implementations, operation 612 can be performed by a notification component the same as or substantially similar to the notification component 410 described and illustrated herein.

At 614, the first notification generated at 612 can be transmitted to a healthcare facility and/or a law enforcement agency. In some implementations, operation 614 can be performed by a communication component the same as or substantially similar to the communication component 412 described and illustrated herein.

Figure 7:
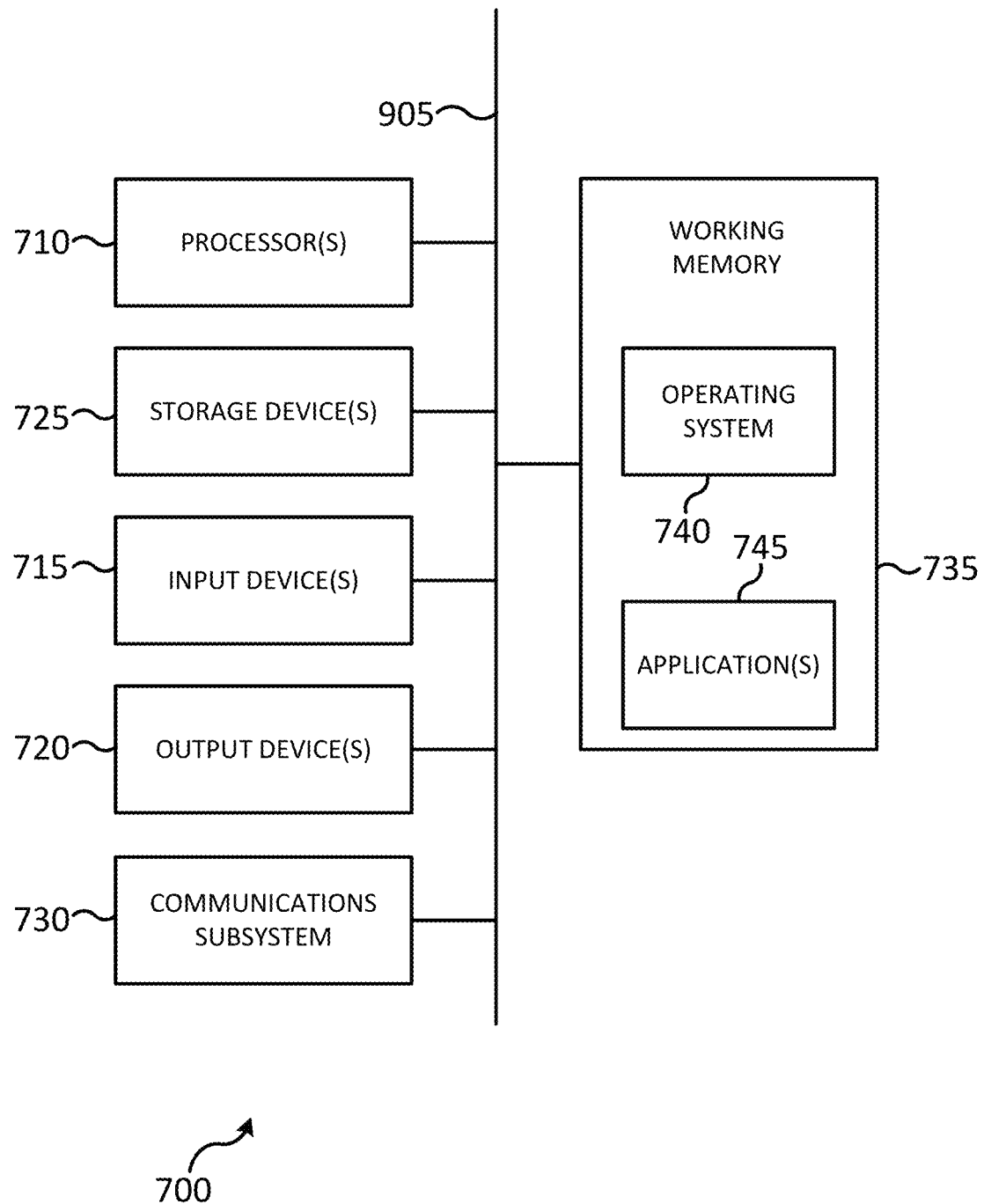
FIG. 7 illustrates a simplified computer system, according to an exemplary embodiment of the present disclosure.

FIG. 7 illustrates a simplified computer system, according to an exemplary embodiment of the present disclosure. A computer system 700 as illustrated in FIG. 7 may be incorporated into devices such as a portable electronic device, mobile phone, or other device as described herein. FIG. 7 provides a schematic illustration of one embodiment of a computer system 700 that can perform some or all of the steps of the methods provided by various embodiments. It should be noted that FIG. 7 is meant only to provide a generalized illustration of various components, any or all of which may be utilized as appropriate. FIG. 7, therefore, broadly illustrates how individual system elements may be implemented in a relatively separated or relatively more integrated manner.

The computer system 700 is shown comprising hardware elements that can be electrically coupled via a bus 705, or may otherwise be in communication, as appropriate. The hardware elements may include one or more processors 710, including without limitation one or more general-purpose processors and/or one or more special-purpose processors such as digital signal processing chips, graphics acceleration processors, and/or the like; one or more input devices 715, which can include without limitation a mouse, a keyboard, a camera, and/or the like; and one or more output devices 720, which can include without limitation a display device, a printer, and/or the like.

The computer system 700 may further include and/or be in communication with one or more non-transitory storage devices 725, which can comprise, without limitation, local and/or network accessible storage, and/or can include, without limitation, a disk drive, a drive array, an optical storage device, a solid-state storage device, such as a random access memory ("RAM"), and/or a read-only memory ("ROM"), which can be programmable, flash-updateable, and/or the like. Such storage devices may be configured to implement any appropriate data stores, including without limitation, various file systems, database structures, and/or the like.

The computer system 700 might also include a communications subsystem 730, which can include without limitation a modem, a network card (wireless or wired), an infrared communication device, a wireless communication device, and/or a chipset such as a Bluetooth™ device, an 802.11 device, a WiFi device, a WiMax device, cellular communication facilities, etc., and/or the like. The communications subsystem 730 may include one or more input and/or output communication interfaces to permit data to be exchanged with a network such as the network described below to name one example, other computer systems, television, and/or any other devices described herein. Depending on the desired functionality and/or other implementation concerns, a portable electronic device or similar device may communicate image and/or other information via the communications subsystem 730. In other embodiments, a portable electronic device, e.g. the first electronic device, may be incorporated into the computer system 700, e.g., an electronic device as an input device 715. In some embodiments, the computer system 700 will further comprise a working memory 735, which can include a RAM or ROM device, as described above.

The computer system 700 also can include software elements, shown as being currently located within the working memory 735, including an operating system 740, device drivers, executable libraries, and/or other code, such as one or more application programs 745, which may comprise computer programs provided by various embodiments, and/or may be designed to implement methods, and/or configure systems, provided by other embodiments, as described herein. Merely by way of example, one or more procedures described with respect to the methods discussed above, such as those described in relation to FIG. 7, might be implemented as code and/or instructions executable by a computer and/or a processor within a computer; in an aspect, then, such code and/or instructions can be used to configure and/or adapt a general purpose computer or other device to perform one or more operations in accordance with the described methods.

A set of these instructions and/or code may be stored on a non-transitory computer-readable storage medium, such as the storage device(s) 725 described above. In some cases, the storage medium might be incorporated within a computer system, such as computer system 700. In other embodiments, the storage medium might be separate from a computer system e.g., a removable medium, such as a compact disc, and/or provided in an installation package, such that the storage medium can be used to program, configure, and/or adapt a general purpose computer with the instructions/code stored thereon. These instructions might take the form of executable code, which is executable by the computer system 700 and/or might take the form of source and/or installable code, which, upon compilation and/or installation on the computer system 700 e.g., using any of a variety of generally available compilers, installation programs, compression/decompression utilities, etc., then takes the form of executable code.

It will be apparent to those skilled in the art that substantial variations may be made in accordance with specific requirements. For example, customized hardware might also be used, and/or particular elements might be implemented in hardware, software including portable software, such as applets, etc., or both. Further, connection to other computing devices such as network input/output devices may be employed.

As mentioned above, in one aspect, some embodiments may employ a computer system such as the computer system 700 to perform methods in accordance with various embodiments of the technology. According to a set of embodiments, some or all of the procedures of such methods are performed by the computer system 700 in response to processor 710 executing one or more sequences of one or more instructions, which might be incorporated into the operating system 740 and/or other code, such as an application program 745, contained in the working memory 735. Such instructions may be read into the working memory 735 from another computer-readable medium, such as one or more of the storage device(s) 725. Merely by way of example, execution of the sequences of instructions contained in the working memory 735 might cause the processor(s) 710 to perform one or more procedures of the methods described herein. Additionally or alternatively, portions of the methods described herein may be executed through specialized hardware.

The terms "machine-readable medium" and "computer-readable medium," as used herein, refer to any medium that participates in providing data that causes a machine to operate in a specific fashion. In an embodiment implemented using the computer system 700, various computer-readable media might be involved in providing instructions/code to processor(s) 710 for execution and/or might be used to store and/or carry such instructions/code. In many implementations, a computer-readable medium is a physical and/or tangible storage medium. Such a medium may take the form of a non-volatile media or volatile media. Non-volatile media include, for example, optical and/or magnetic disks, such as the storage device(s) 725. Volatile media include, without limitation, dynamic memory, such as the working memory 735.

Common forms of physical and/or tangible computer-readable media include, for example, a floppy disk, a flexible disk, hard disk, magnetic tape, or any other magnetic medium, a CD-ROM, any other optical medium, punchcards, papertape, any other physical medium with patterns of holes, a RAM, a PROM, EPROM, a FLASH-EPROM, any other memory chip or cartridge, or any other medium from which a computer can read instructions and/or code.

Various forms of computer-readable media may be involved in carrying one or more sequences of one or more instructions to the processor(s) 710 for execution. Merely by way of example, the instructions may initially be carried on a magnetic disk and/or optical disc of a remote computer. A remote computer might load the instructions into its dynamic memory and send the instructions as signals over a transmission medium to be received and/or executed by the computer system 700.

The communications subsystem 730 and/or components thereof generally will receive signals, and the bus 705 then might carry the signals and/or the data, instructions, etc. carried by the signals to the working memory 735, from which the processor(s) 710 retrieves and executes the instructions. The instructions received by the working memory 735 may optionally be stored on a non-transitory storage device 725 either before or after execution by the processor(s) 710.

The methods, systems, and devices discussed above are examples. Various configurations may omit, substitute, or add various procedures or components as appropriate. For instance, in alternative configurations, the methods may be performed in an order different from that described, and/or various stages may be added, omitted, and/or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Specific details are given in the description to provide a thorough understanding of exemplary configurations including implementations. However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Also, configurations may be described as a process which is depicted as a schematic flowchart or block diagram. Although each may describe the operations as a sequential process, many of the operations can be performed in parallel or concurrently. In addition, the order of the operations may be rearranged. A process may have additional steps not included in the figure. Furthermore, examples of the methods may be implemented by hardware, software, firmware, middleware, microcode, hardware description languages, or any combination thereof. When implemented in software, firmware, middleware, or microcode, the program code or code segments to perform the necessary tasks may be stored in a non-transitory computer-readable medium such as a storage medium. Processors may perform the described tasks.

Having described several example configurations, various modifications, alternative constructions, and equivalents may be used without departing from the spirit of the disclosure. For example, the above elements may be components of a larger system, wherein other rules may take precedence over or otherwise modify the application of the technology. Also, a number of steps may be undertaken before, during, or after the above elements are considered. Accordingly, the above description does not bind the scope of the claims.

As used herein and in the appended claims, the singular forms "a", "an", and "the" include plural references unless the context clearly dictates otherwise. Thus, for example, reference to "a user" includes a plurality of such users, and reference to "the processor" includes reference to one or more processors and equivalents thereof known to those skilled in the art, and so forth.

Also, the words "comprise", "comprising", "contains", "containing", "include", "including", and "includes", when used in this specification and in the following claims, are intended to specify the presence of stated features, integers, components, or steps, but they do not preclude the presence or addition of one or more other features, integers, components, steps, acts, or groups.

What is claimed is:

1. A method for monitoring one or more physical conditions of an operator of a driving apparatus to improve safety, the method being implemented by a server comprising one or more of a processor configured to execute machine-readable instructions, the method comprising:
managing user information for a plurality of operators including a first operator;
obtaining, via a communications network, from a driving apparatus associated with the first operator, real-time driving information regarding the driving apparatus being currently operated by the first operator, the real-time driving information including a first status indicating a physical condition of the first operator while currently operating the driving apparatus, wherein the real-time driving information regarding the first operator further includes a second status indicating a electrocardiogram (EKG) device within the driving apparatus associated with the first operator has been disconnected from the first operator for more than a predetermined time period by virtue of no signals have been received from the EKG device for the predetermined time period, and the real-time driving information includes a location of the driving apparatus, wherein the first status is separate and distinct from the second status;
determining, for the first operator, whether the physical condition of the first operator has breached a predetermined threshold;
when it is determined that the physical condition of the first operator has breached the predetermined threshold;
determining a risk level posed by the first operator based on the physical condition of the first operator, the risk level indicating a level of danger to public safety posed by the current operation of the driving apparatus by the first operator;
based on the determined risk level posed by the first operator, obtaining a current location of the driving apparatus associated with the first operator;
generating a first notification for indicating the risk level posed by current operation of the driving apparatus by the first operator, the first notification indicating the identity of the first operator and the current location of the driving apparatus associated with the first operator, the first notification describing the first operator suffers an abnormal physical condition; and
transmitting the first notification to a data receiver in a healthcare facility or to a data receiver in a law enforcement agency; and, wherein
obtaining the current location of the driving apparatus associated with the first operator comprises:
transmitting an identification of the driving apparatus associated with the first operator to an unmanned vehicle for locating the driving apparatus associated with the first operator;
transmitting the location of the driving apparatus as received in the real-time driving information to the unmanned vehicle; and
receiving location information indicating the current location of the driving apparatus associated with the first operator from the unmanned vehicle.

2. The method of claim 1, wherein the first status is based on electrocardiogram (EKG) signals and/or electroencephalography (EEG) signals generated within the first driving apparatus.

3. The method of claim 1, wherein the first status is based on a body temperature signal and/or a blood alcohol content (BAC) signal generated within the first driving apparatus.

4. The method of claim 1, wherein the first status is based on an eye movement signal generated within the first driving apparatus.

5. The method of claim 1, wherein determining the risk level posed by the first operator based on the physical condition of the first operator comprises:
obtaining information regarding a medical history, a driving history, and/or a criminal history of the first operator; and
determining the risk level posed by the first operator based on the obtained information regarding the medical history, the driving history, and/or the criminal history of the first operator.

6. The method of claim 5, further comprising determining whether to transmit the first notification to the data receiver in the healthcare facility or the data receiver in the law enforcement agency based on the risk level determined.

7. The method of claim 1, further comprising receiving updated location information regarding the driving apparatus associated with the first operator from the unmanned vehicle, and transmitting the updated location information regarding the driving apparatus associated with the first operator to the healthcare facility or the law enforcement agency.

8. The method of claim 1, wherein,
the plurality of operators further includes a second operator;
obtaining, via the communications network, from a driving apparatus associated with the second operator, real-time driving information regarding the driving apparatus associated with the second operator being currently operated by the second operator, the real-time driving information including a third status indicating a physical condition of the second operator while operating the driving apparatus associated with the second operator;
determining, for the second operator, whether the physical condition of the second operator has breached the predetermined threshold;
when it is determined that the physical condition of the second operator has breached a predetermined threshold:
determining a risk level posed by the second operator based on the physical condition of the second operator, the risk level indicating a level of danger to public safety posed by the current operation of the driving apparatus associated with the second operator by the second operator;
obtaining a current location of the driving apparatus associated with the second operator;
generating a second notification based on the second status, the second notification indicating the identity of the second operator and the current location of the driving apparatus associated with the second operator, the second notification describing the second operator suffers an abnormal physical condition; and
transmitting the second notification to the data receiver in the healthcare facility or to the data receiver in the law enforcement agency.

9. The method of claim 1, wherein the physical condition includes cardiac activities, brain activities, a body temperature, a blood alcohol content level, and/or any eye movement of the first operator.

10. A system for monitoring one or more physical conditions of an operator of a driving apparatus to improve safety, the system comprising a server comprising one or more processors configured to execute machine-readable instructions, wherein the one or more processors are configured to perform:
managing user information for a plurality of operators including a first operator;
obtaining, via a communications network, from a driving apparatus associated with the first operator, real-time driving information regarding the driving apparatus being currently operated by the first operator, the real-time driving information including a first status indicating a physical condition of the first operator while currently operating the driving apparatus, wherein the real-time driving information regarding the first operator further includes a second status indicating a electrocardiogram (EKG) device within the driving apparatus associated with the first operator has been disconnected from the first operator for more than a predetermined time period by virtue of no signals have been received from the EKG device for the predetermined time period, the sensing device being configured to detect a heart condition of the first operator, wherein the first status is separate and distinct from the second status;
determining, for the first operator, whether the physical condition of the first operator has breached a predetermined threshold;
when it is determined that the physical condition of the first operator has breached a predetermined threshold:
determining a risk level posed by the first operator based on the physical condition of the first operator, the risk level indicating a level of danger to public safety posed by the current operation of the driving apparatus by the first operator;
based on the determined risk level posed by the first operator, obtaining a current location of the driving apparatus associated with the first operator;
generating a first notification based on the first status, the first notification indicating the identity of the first operator and the current location of the driving apparatus associated with the first operator, the first notification describing the first operator suffers an abnormal physical condition; and
transmitting the first notification to a data receiver in a healthcare facility or to a data receiver in a law enforcement agency; and, wherein
obtaining the current location of the driving apparatus associated with the first operator comprises:
transmitting an identification of the driving apparatus associated with the first operator to an unmanned vehicle for locating the driving apparatus associated with the first operator;
transmitting the location of the driving apparatus as received in the real-time driving information to the unmanned vehicle; and
receiving location information indicating the current location of the driving apparatus associated with the first operator from the unmanned vehicle.

11. The system of claim 10, wherein the first status is based on electrocardiogram (EKG) signals and/or electroencephalography (EEG) signals generated within the first driving apparatus.

12. The system of claim 10, wherein the first status is based on a body temperature signal and/or a blood alcohol content (BAC) signal generated within the first driving apparatus.

13. The system of claim 10, wherein the first status is based on an eye movement signal generated within the first driving apparatus.

14. The system of claim 10, wherein determining the risk level posed by the first operator based on the physical condition of the first operator comprises:
obtaining information regarding a medical history, a driving history, and/or a criminal history of the first operator; and, wherein the method further comprises
determining the risk level posed by the first operator based on the obtained information regarding the medical history, the driving history, and/or the criminal history of the first operator.

15. The system of claim 14, wherein the processors are further configured to perform determining whether to transmit the first notification to the data receiver in the healthcare facility or the data receiver in the law enforcement agency based on the risk level determined.

16. The system of claim 10, the processors are further configured to perform:

transmitting a last known location of the driving apparatus associated with the first operator to the unmanned vehicle, receiving updated location information regarding the driving apparatus associated with the first operator from the unmanned vehicle, and transmitting the updated location information regarding the driving apparatus associated with the first operator to the healthcare facility or the law enforcement agency.

17. The system of claim 10, wherein the plurality of operators further includes a second operator;

obtaining, via the communications network, from a driving apparatus associated with the second operator, real-time driving information regarding the driving apparatus associated with the second operator being currently operated by the second operator, the real-time driving information including a third status indicating a physical condition of the second operator while operating the driving apparatus associated with the second operator;

determining, for the second operator, whether the physical condition of the second operator has breached the predetermined threshold;

when it is determined that the physical condition of the second operator has breached a predetermined threshold:

determining a risk level posed by the second operator based on the physical condition of the second operator, the risk level indicating a level of danger to public safety posed by the current operation of the driving apparatus associated with the second operator by the second operator;

obtaining a current location of the driving apparatus associated with the second operator;

generating a second notification based on the second status, the second notification indicating the identity of the second operator and the current location of the driving apparatus associated with the second operator, the second notification describing the second operator suffers an abnormal physical condition; and transmitting the second notification to the data receiver in the healthcare facility or to the data receiver in the law enforcement agency.

18. The system of claim 10, wherein the physical condition includes cardiac activities, brain activities, a body temperature, a blood alcohol content level, and/or any eye movement of the first operator.

* * * * *